(12) United States Patent
Liu et al.

(10) Patent No.: US 9,138,190 B2
(45) Date of Patent: Sep. 22, 2015

(54) WAVY PHYSIOLOGICAL SIGNAL COLLECTING DEVICE AND WAVY PHYSIOLOGICAL SIGNAL COLLECTING MATTRESS

(75) Inventors: Xufang Liu, Shenzhen (CN); Xuan Tang, Shenzhen (CN)

(73) Assignee: SHENZHEN SEELEN TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 14/241,085

(22) PCT Filed: Jun. 15, 2012

(86) PCT No.: PCT/CN2012/076957
§ 371 (c)(1),
(2), (4) Date: Feb. 26, 2014

(87) PCT Pub. No.: WO2013/029408
PCT Pub. Date: Mar. 7, 2013

(65) Prior Publication Data
US 2014/0213877 A1 Jul. 31, 2014

(30) Foreign Application Priority Data
Aug. 31, 2011 (CN) .......................... 2011 1 0255641

(51) Int. Cl.
| | |
|---|---|
| *A61B 5/117* | (2006.01) |
| *A61B 5/00* | (2006.01) |
| *A61B 5/024* | (2006.01) |
| *A61B 5/08* | (2006.01) |
| *A61B 5/11* | (2006.01) |

(52) U.S. Cl.
CPC ........... *A61B 5/6831* (2013.01); *A61B 5/02444* (2013.01); *A61B 5/0803* (2013.01); *A61B 5/1126* (2013.01); *A61B 5/6892* (2013.01); *A61B 2562/0247* (2013.01); *A61B 2562/164* (2013.01)

(58) Field of Classification Search
CPC ....................................................... A61B 5/00
USPC .................................. 600/587, 595, 300, 301
See application file for complete search history.

(56) References Cited

U.S. PATENT DOCUMENTS

| | | | |
|---|---|---|---|
| 3,926,177 A * | 12/1975 | Hardway et al. ............... | 600/535 |
| 3,996,922 A * | 12/1976 | Basham ........................ | 600/535 |
| 4,665,926 A * | 5/1987 | Leuner et al. ................. | 600/529 |
| 5,148,706 A * | 9/1992 | Masuda et al. ................. | 73/172 |
| 5,808,552 A * | 9/1998 | Wiley et al. ................ | 340/573.4 |
| 5,902,255 A * | 5/1999 | Ogino ........................... | 600/595 |
| 6,450,957 B1 * | 9/2002 | Yoshimi et al. ............... | 600/309 |

(Continued)

*Primary Examiner* — Rene Towa
*Assistant Examiner* — May Abouelela

(57) ABSTRACT

The present disclosure provides a wavy physiological signal collecting device and a physiological signal collecting mattress. The device includes a wavy flexible body including a flexible body panel and a plurality of protruding flexible bodies each of which is arranged on the flexible body panel for converting a human body pressure applied thereto to a tensile force; a tensile force sensor arranged in the flexible body panel for generating an electrical signal according to the tensile force; and a signal processing unit configured for processing the electrical signal to obtain a human body physiological signal. The wavy flexible body converts the human body pressure to an electrical signal and processes the electrical signal, thereby obtaining the human body physiological signal in daily life without directly contacting human skin, allowing the physiological signal to be obtained more conveniently.

7 Claims, 3 Drawing Sheets

(56) References Cited

U.S. PATENT DOCUMENTS

| | | | |
|---|---|---|---|
| 6,468,234 B1* | 10/2002 | Van der Loos et al. | 600/595 |
| 6,493,568 B1* | 12/2002 | Bell et al. | 600/323 |
| 6,778,090 B2* | 8/2004 | Newham | 340/573.1 |
| 7,183,930 B2* | 2/2007 | Basir et al. | 340/573.1 |
| 7,431,700 B2* | 10/2008 | Aoki et al. | 600/534 |
| 7,603,217 B2* | 10/2009 | Plocher et al. | 701/45 |
| 7,650,803 B2* | 1/2010 | Ando et al. | 73/862.391 |
| 7,883,478 B2* | 2/2011 | Skinner et al. | 600/595 |
| 8,075,499 B2* | 12/2011 | Nathan et al. | 600/587 |
| 8,123,685 B2* | 2/2012 | Brauers et al. | 600/301 |
| 8,272,892 B2* | 9/2012 | McNeely et al. | 439/577 |
| 8,419,660 B1* | 4/2013 | Shaw | 600/595 |
| 8,672,842 B2* | 3/2014 | Kenalty et al. | 600/300 |
| 8,752,220 B2* | 6/2014 | Soderberg et al. | 5/600 |
| 2003/0216670 A1* | 11/2003 | Beggs | 600/595 |
| 2003/0233034 A1* | 12/2003 | Varri et al. | 600/301 |
| 2004/0236202 A1* | 11/2004 | Burton | 600/384 |
| 2005/0096559 A1* | 5/2005 | Yanai | 600/534 |
| 2005/0107722 A1* | 5/2005 | Ozaki et al. | 600/587 |
| 2005/0148904 A1* | 7/2005 | Mimura et al. | 600/587 |
| 2006/0076103 A1* | 4/2006 | Clarke | 156/229 |
| 2006/0084855 A1* | 4/2006 | Teschner et al. | 600/390 |
| 2006/0112489 A1* | 6/2006 | Bobey et al. | 5/655.3 |
| 2006/0129047 A1* | 6/2006 | Ruotoistenmaki | 600/483 |
| 2007/0112283 A1* | 5/2007 | Ando et al. | 600/587 |
| 2007/0118054 A1* | 5/2007 | Pinhas et al. | 600/587 |
| 2008/0132808 A1* | 6/2008 | Lokhorst et al. | 600/595 |
| 2009/0062693 A1* | 3/2009 | Woolfson et al. | 600/587 |
| 2009/0287120 A1* | 11/2009 | Ferren et al. | 600/587 |
| 2010/0174198 A1* | 7/2010 | Young et al. | 600/484 |
| 2010/0174199 A1* | 7/2010 | Young et al. | 600/484 |
| 2010/0268121 A1* | 10/2010 | Kilborn | 600/587 |
| 2011/0009776 A1* | 1/2011 | Woolfson et al. | 600/587 |
| 2011/0245732 A1* | 10/2011 | Mravyan et al. | 600/587 |
| 2011/0251522 A1* | 10/2011 | Fujita et al. | 600/587 |
| 2011/0319787 A1* | 12/2011 | Lamoise et al. | 600/549 |
| 2012/0053424 A1* | 3/2012 | Kenalty et al. | 600/300 |
| 2012/0259181 A1* | 10/2012 | Fujita et al. | 600/300 |
| 2012/0299730 A1* | 11/2012 | Rahimi | 340/573.1 |

\* cited by examiner

WAVY PHYSIOLOGICAL SIGNAL COLLECTING DEVICE AND WAVY PHYSIOLOGICAL SIGNAL COLLECTING MATTRESS

BACKGROUND

1. Technical Field

The present disclosure generally relates to technologies of collecting physiological signals, and more particularly, to a wavy physiological signal collecting device and a wavy physiological signal collecting mattress.

2. Description of Related Art

A conventional collecting device of a human body physiological signal needs to be in tight contact with human skin for collecting pressure signals generated by muscles and converting the pressure signals to electrical signals to obtain important human body physiological signals such as heartbeat signals, respiration signals, and convulsion signals.

The above collecting device needs to be in tight contact with human skin in the process of collecting the physiological signal, which is inconvenient to the user. Meanwhile, since a signal electrode of the collecting device needs to be adhered to human skin, different resistances may be generated caused by various reasons including that the signal electrode is adhered to a different position on human skin each time, which results in unstable strengths (magnitudes) of the collected signals and prevents the collecting device from collecting needed physiological signals such as the strength information of the heartbeat.

SUMMARY

The main object of the present disclosure is to provide a wavy physiological signal collecting device which improves the convenience of collecting the physiological signal.

The wavy physiological signal collecting device provided in the present disclosure includes a wavy flexible body and a signal processing unit;

the wavy flexible body includes a flexible body panel and a plurality of protruding flexible bodies each of which is arranged on the flexible body panel for converting a human body pressure applied thereto to a tensile force; and a tensile force sensor arranged in the flexible body panel for generating an electrical signal according to the tensile force; and the signal processing unit is configured for processing the electrical signal to obtain a corresponding human body physiological signal.

Preferably, the protruding flexible bodies are respectively spacedly arranged on an upper surface and a lower surface of the flexible body panel to form a panel of the wavy flexible body.

Preferably, the tensile force sensor is arranged in a spacing area between two adjacent protruding flexible bodies.

Preferably, the signal processing unit includes a signal amplifying circuit for amplifying an analog electrical signal, a filtering circuit for filtering the amplified analog electrical signal to obtain the human body physiological signal, and an A/D conversion circuit for converting the filtered analog electrical signal to a digital signal.

Preferably, the device further includes a wireless through transmission circuit for transmitting the digital signal through wireless unvarnished transmission.

Preferably, the device further includes a power supply unit for supplying power and a power supply management unit for managing the power supply unit.

Preferably, the power supply unit includes a battery.

The present disclosure further provides a physiological signal collecting mattress, including at least two wavy physiological signal collecting devices and a wireless through transmission circuit;

each of the at least two wavy physiological signal collecting devices includes a wavy flexible body including a flexible body panel and a plurality of protruding flexible bodies each of which is arranged on the flexible body panel for converting a human body pressure applied thereto to a tensile force; a tensile force sensor arranged in the flexible body panel for generating an electrical signal according to the tensile force; and a signal processing unit configured for processing the electrical signal to obtain a corresponding human body physiological signal; and the wireless through transmission circuit is configured for transmitting the electrical signal through wireless unvarnished transmission.

Preferably, the protruding flexible bodies are respectively spacedly arranged on an upper surface and a lower surface of the flexible body panel to form a panel of the wavy flexible body.

Preferably, the tensile force sensor is arranged in a spacing area between two adjacent protruding flexible bodies.

The present disclosure yet further provides a physiological signal collecting mattress including at least two wavy physiological signal collecting devices and a wireless through transmission circuit;

each of the at least two wavy physiological signal collecting devices includes a wavy flexible body including a flexible body panel and a plurality of protruding flexible bodies each of which is arranged on the flexible body panel for converting a human body pressure applied thereto to a tensile force; a tensile force sensor arranged in the flexible body panel for generating an electrical signal according to the tensile force; and a signal processing unit configured for processing the electrical signal to obtain a corresponding human body physiological signal;

the flexible body is configured as a piece and the flexible body panel and the protruding flexible bodies are integrally formed;

the flexible body panel is elongated and at least includes an upper surface and a lower surface, and the protruding flexible bodies being respectively arranged on the upper surface and the lower surface; and the unvarnished transmission circuit is configured for transmitting a digital signal of the electrical signal through unvarnished transmission.

Preferably, the protruding flexible bodies are respectively spacedly arranged on the upper surface and the lower surface of the flexible body panel to form a wavy flexible body panel.

Preferably, the tensile force sensor is arranged in a spacing area between two adjacent protruding flexible bodies.

With the wavy flexible body converting the human body pressure to an electrical signal and processes the electrical signal, the present disclosure can obtain the human body physiological signal in daily life without directly contacting human skin, allowing the physiological signal to be obtained more conveniently. Meanwhile, the obtained physiological signal is transmitted to a remote device by using wireless technology to separate the collection of the signal from the further analysis and unified storage of the signal, which further facilitates the collection of the physiological signal.

DESCRIPTION OF THE DRAWINGS

Many aspects of the embodiments can be better understood with reference to the following drawings. The components in the drawings are not necessarily dawns to scale, the emphasis instead being placed upon clearly illustrating the principles of the embodiments. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment is this disclosure are not necessarily to the same embodiment, and such references mean at least one.

Figure 1:
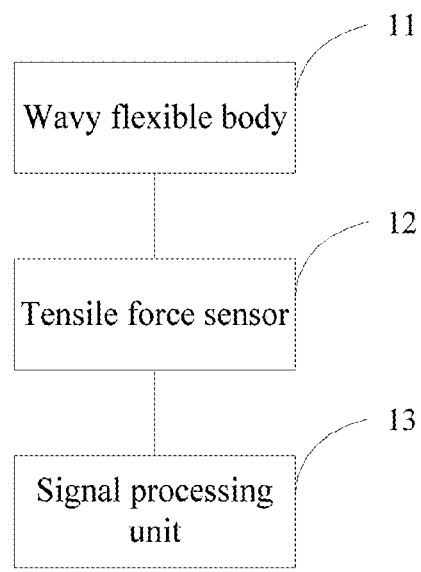
FIG. 1 is a partially schematic view of a wavy physiological signal collecting device in accordance with an embodiment of the present disclosure.

Referring to FIG. 1, a wavy physiological signal collecting device in accordance with an embodiment of the present disclosure is provided. The device includes a wavy flexible body 11, a tensile force sensor 12, and a signal processing unit 13.

Figure 3:
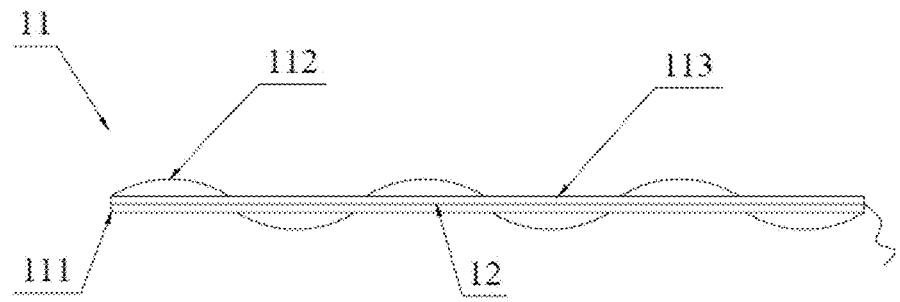
FIG. 3 is a cross-sectional view of the physical structure of the wavy flexible body of the wavy physiological signal collecting device in accordance with an embodiment of the present disclosure.

The wavy flexible body 11 includes a flexible body panel 111 and a plurality of protruding flexible bodies 112 each of which is arranged on the flexible body panel 111 (referring to FIG. 3) for converting a human body pressure applied thereto to a tensile force. The tensile force sensor 12 is arranged in the flexible body panel 111 for generating an electrical signal according to the tensile force. The signal processing unit 13 processes the electrical signal to obtain the corresponding human body physiological signal. The physiological signal includes a respiration signal, a heartbeat signal, a convulsion signal, and a motion signal, etc.

In the actual manufacture of the above device, the wavy flexible body 11 may be formed as a piece, and the flexible body panel 111 and the protruding flexible bodies 112 are integrally formed and are separatedly described for easy description in the above disclosure.

Figure 2:
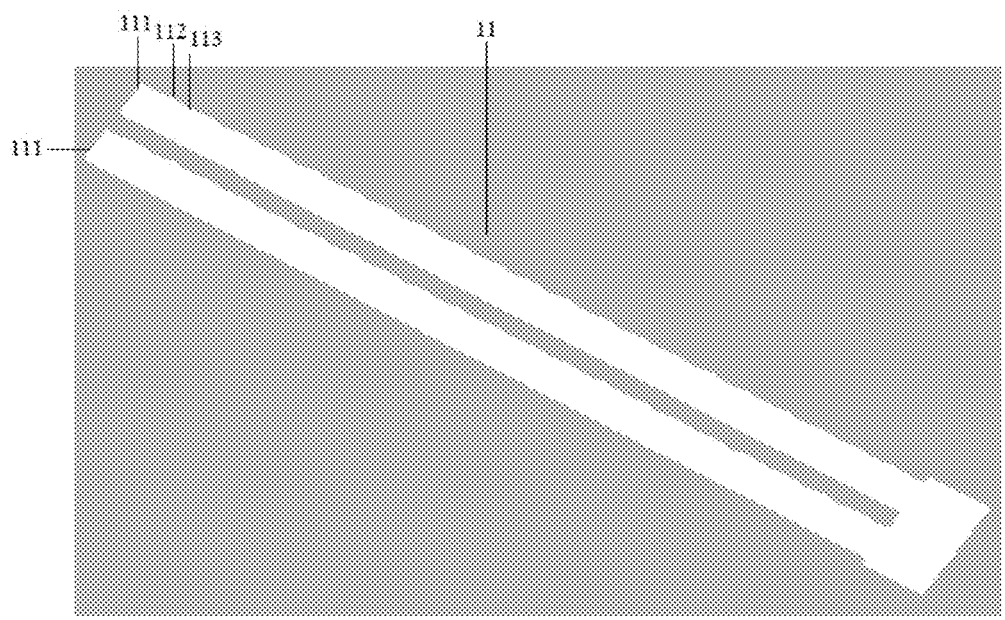
FIG. 2 is a schematic view of a physical structure of a wavy flexible body of the wavy physiological signal collecting device in accordance with an embodiment of the present disclosure.

Referring to FIG. 2, supposed that the flexible body panel 111 is elongated, the elongated flexible body panel 111 at least includes an upper surface and a lower surface, and the protruding flexible bodies 112 are respectively arranged on the upper surface and the lower surface. Each of the protruding flexible bodies 112 can be strip shaped and parallel with a width of the elongated flexible body panel 111. A spacing area is defined between two adjacent protruding flexible bodies 112. The spacing area 113 between each two adjacent protruding flexible bodies 112 is a relatively-recessed area due to the two protruding flexible bodies 112. The upper surface and the lower surface of the flexible body panel 111 are respectively provided with the protruding flexible bodies 112 and the spacing areas 113. Each spacing area 113 located on the upper surface corresponds to a protruding flexible body 112 located on the lower surface, and each flexible body 112 located on the upper surface corresponds to a corresponding spacing area 113 located on the lower surface, thereby forming the panel of the wavy flexible body 11. A cross-sectional view of each protruding flexible body 112 can be a curved surface. Due to the above arranging way of the protruding flexible bodies 112 on the upper surface and the lower surface, curved surfaces of the protruding flexible bodies 112 located on the upper surface are capable of cooperating with the curved surfaces of the protruding flexible bodies 112 located on the lower surface to form a similar "sinusoid" symmetrically centered on the flexible body panel 111.

In this way, if a human body pressure is applied to a corresponding protruding flexible body 112, since the protruding flexible body 112 is arranged corresponding to the spacing area 113, the protruding flexible body 112 applies a tensile force to the flexible body panel 111 of the corresponding spacing area 113, that is, the human body pressure applied to the protruding flexible body 112 is converted to a tensile force. The tensile force sensor 12 can be arranged in the spacing area 113 of the flexible body panel 111 (referring to FIG. 3) for generating an electrical signal according to the converted tensile force. The electrical signal is generally an analog signal.

The wavy flexible body 11 can be arranged in daily items such as mattresses, seat cushions, back cushions, and foot pads for obtaining a body pressure of a user who is using the corresponding daily item. Since a wavy area of the wavy flexible body 11 can convert the human body pressure applied thereto to a tensile force, thus, the wavy flexible body 11 can be used for converting the human body pressure to the tensile force. Thus, a user can use the wavy flexible body 11 anytime and anywhere, which is very convenient.

Figure 4:
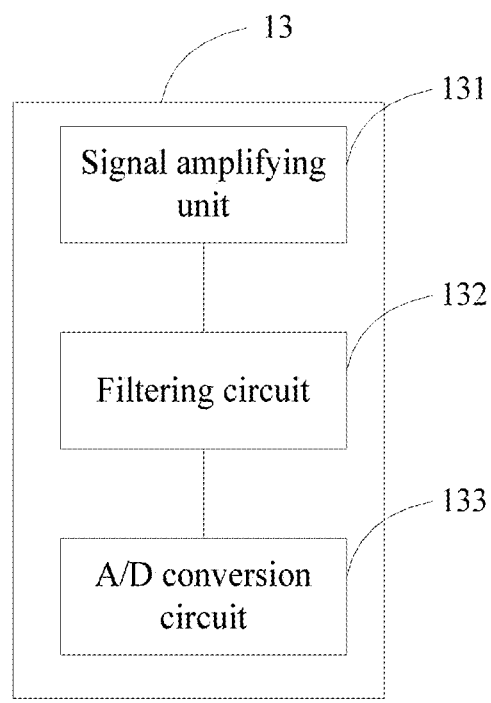
FIG. 4 is a schematic view of a signal processing unit of the wavy physiological signal collecting device in accordance with an embodiment of the present disclosure.

Referring to FIG. 4, the signal processing unit 13 includes a signal amplifying circuit 131, a filtering circuit 132, and an A/D conversion circuit 133. The signal amplifying circuit 131 amplifies the analog signal, the filtering circuit 132 filters the amplified analog signal to obtain the needed human body physiological signal, and the A/D conversion circuit 133 converts the filtered analog signal to a digital signal.

The signal amplifying circuit 131 can be connected to the corresponding tensile force sensor 12 for amplifying the electrical signal generated by the tensile force sensor 12 such that the electrical signal can be thereafter filtered. The amplification degree to which the electrical signal is amplified by the signal amplifying circuit 131 can be determined according to actual requirements.

The filtering circuit 132 can be connected to the signal amplifying circuit 131 for filtering the electrical signal amplified by the signal amplifying circuit 131. Corresponding parameters of the filtering circuit 132 can be set to filter signals having undesired frequencies and obtain needed electrical signals, for example, to filter the signal having a frequency not in the range from 0.7 Hz to 3 Hz and to obtain the needed heartbeat signal (generally having a frequency ranging from 0.7 Hz to 3 Hz). Thus, corresponding parameters of the filtering circuit 132 can be set to allow the filtering circuit 132 to filter undesired electrical signals and obtain needed physiological signals.

The A/D conversion circuit 133 can be connected to the filtering circuit 132 for performing the analog-to-digital conversion to the filtered electrical signal. Since the electrical signal generated by the tensile force sensor 12 is generally an analog signal, the filtered electrical signal is correspondingly an analog signal. The A/D conversion circuit 133 is capable of converting the analog signal to a digital signal for allowing for easy operations such as a further process and transmission of the signal.

Figure 5:
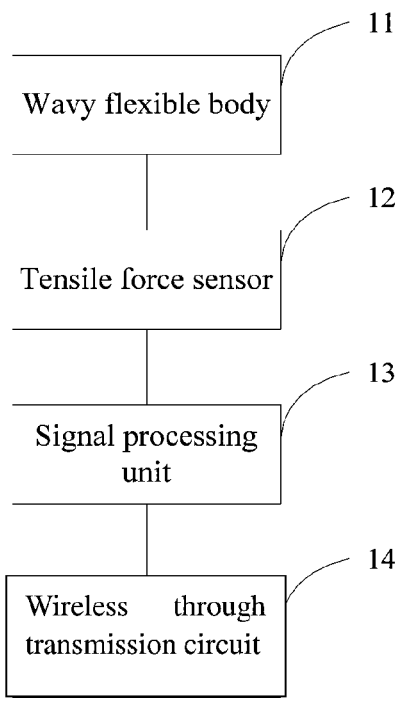
FIG. 5 is a schematic view of a wavy physiological signal collecting device in accordance with another embodiment of the present disclosure.

Referring to FIG. 5, in another embodiment of the present disclosure, the above device further includes a wireless through transmission circuit 14 for transmitting the digital signal through wireless unvarnished transmission.

In order to improve the convenience of the collection of the human body physiological signal, the collection of the physiological signal can be separated from a further analysis and unified storage of the physiological signal. After the needed physiological signal is collected, the wireless through transmission circuit 14 can transmit the physiological signal to a remote device to allow for the further analysis and unified storage of the physiological signal.

The above device further includes a power supply unit (not shown) and a power supply management unit (not shown). The power supply unit is configured for supplying power and the power supply management unit is configured for managing the power supply unit.

The above power supply unit can be a battery for supplying power to the above device. The device manages the power supply unit via the power supply management unit.

The above power supply unit can be a connecting component connected to an external power supply for supplying power to the above device. The above device manages the connecting component via the power supply management unit.

The above wavy physiological signal collecting device converts the human body pressure to an electrical signal and processes the electrical signal via the wavy flexible body 11, thereby obtaining the human body physiological signal without directly contacting human skin, allowing the physiological signal to be obtained more conveniently. Meanwhile, the obtained physiological signal is transmitted to a remote device by using wireless technology to separate the collection of the signal from the further analysis and unified storage of the signal, which further facilitates the collection of the physiological signal.

Figure 6:
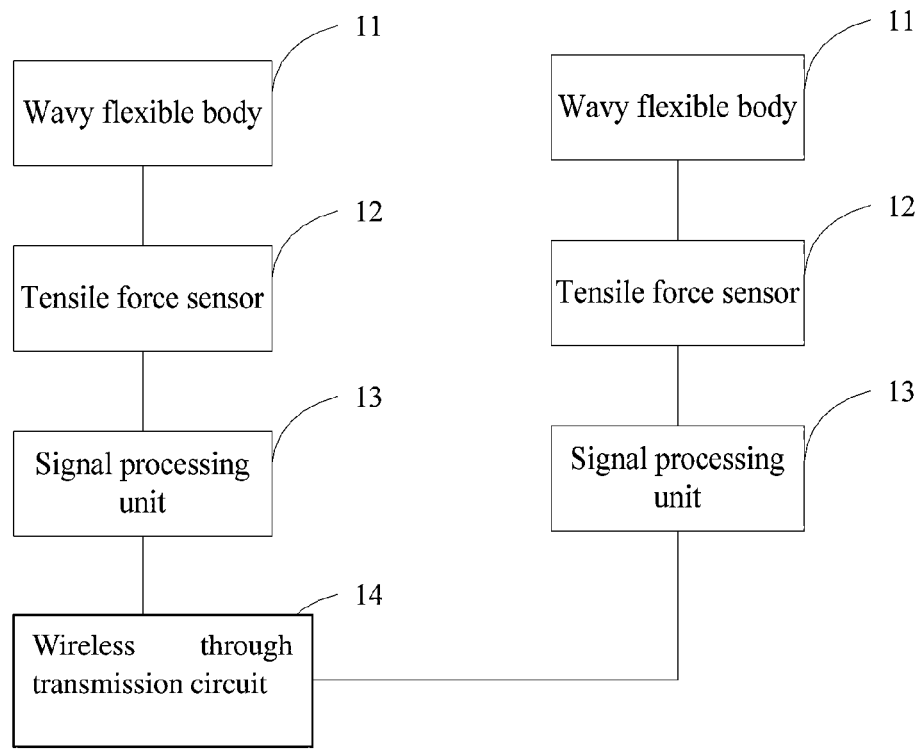
FIG. 6 is a schematic view of a physiological signal collecting mattress in accordance with an embodiment of the present disclosure.

Referring to FIG. 6, a physiological signal collecting mattress in accordance with an embodiment of the present disclosure is provided. The mattress includes at least two wavy physiological signal collecting devices and a wireless through transmission circuit 14.

Each of the wavy physiological signal collecting devices includes a wavy flexible body 11, a tensile force sensor 12, and a signal processing unit 13. The wavy flexible body includes a flexible body panel 111 and a plurality of protruding flexible bodies 112 each of which is arranged on the flexible body panel 111 (shown in FIG. 3) for converting a human pressure applied thereto to a tensile force. The tensile force sensor 12 is arranged in the flexible body panel 111 for generating an electrical signal according to the tensile force. The signal processing unit 13 processes the electrical signal to obtain the corresponding human body physiological signal. The wireless through transmission circuit 14 transmits the digital signal through wireless unvarnished transmission. The physiological signal includes a respiration signal, a heartbeat signal, a convulsion signal, and a motion signal, etc.

In order to save cost, the two or more above wavy physiological signal collecting devices can share one wireless through transmission circuit 14 for transmitting the digital signal.

The signal processing units 13 of the above at least two wavy physiological signal collecting devices can respectively obtain different physiological signals which are respectively transmitted via the wireless through transmission circuit 14. For example, one of the wavy physiological signal collecting devices can obtain the respiration signal, and the other one can obtain the heartbeat signal.

In the actual manufacture of the above mattress, the wavy flexible body 11 may be formed as a piece, and the flexible body panel 111 and the protruding flexible bodies 112 are integrally formed and are separatedly described for easy description in the above disclosure.

Referring to FIG. 2, supposed the flexible body panel 111 is elongated, the elongated flexible body panel 111 at least includes an upper surface and a lower surface, and the protruding flexible bodies 112 are respectively arranged on the upper surface and the lower surface. Each of the protruding flexible bodies 112 can be strip shaped and parallel with a width of the elongated flexible body panel 111. A spacing area is defined between two adjacent protruding flexible bodies 112. The spacing area 113 between each two adjacent protruding flexible bodies 112 is a relatively-recessed area due to the two protruding flexible bodies 112. The upper surface and the lower surface of the flexible body panel 111 are respectively provided with the protruding flexible bodies 112 and the spacing areas 113. Each spacing area 113 located on the upper surface corresponds to a protruding flexible body 112 located on the lower surface, and each flexible body 112 located on the upper surface corresponds to a corresponding spacing area 113 located on the lower surface, thereby forming the panel of the wavy flexible body 11. A cross-sectional view of each protruding flexible body 112 can be a curved surface. Due to the above arranging way of the protruding flexible bodies 112 on the upper surface and the lower surface, curved surfaces of the protruding flexible bodies 112 located on the upper surface are capable of cooperating with the curved surfaces of the protruding flexible bodies 112 located on the lower surface to form a similar "sinusoid" symmetrically centered on the flexible body panel 111.

In this way, if a human body pressure is applied to a corresponding protruding flexible body 112, since the protruding flexible body 112 is arranged corresponding to the spacing area 113, the protruding flexible body 112 applies a tensile force to the flexible body panel 111 of the spacing area 113, that is, the human body pressure applied to the protruding flexible body 112 is converted to a tensile force. The tensile force sensor 12 can be arranged in the spacing area 113 of the corresponding flexible body panel 111 (referring to in FIG. 3) for generating an electrical signal according to the converted tensile force. The electrical signal is generally an analog signal.

The wavy flexible body 11 can be arranged in daily items such as mattresses, seat cushions, back cushions, and foot pads for obtaining a body pressure of a user who is using the corresponding daily item. Since wavy areas of the wavy flexible body 11 can convert the human body pressure applied thereto to a tensile force, thus, the wavy flexible body 11 can be used for converting the human body pressure to the tensile force. Thus, a user can use the wavy flexible body 11 anytime and anywhere, which is very convenient.

Referring to FIG. 4, the signal processing unit 13 includes a signal amplifying circuit 131, a filtering circuit 132, and an A/D conversion circuit 133. The signal amplifying circuit 131 amplifies the analog signal, the filtering circuit 132 filters the amplified analog signal to obtain the needed human body physiological signal, and the A/D conversion circuit 133 converts the filtered analog signal to a digital signal.

The signal amplifying circuit 131 can be connected to the corresponding tensile force sensor 12 for amplifying the electrical signal generated by the tensile force sensor 12 such that the electrical signal can be thereafter filtered. The amplification degree to which the electrical signal is amplified by the signal amplifying circuit 131 can be determined according to actual requirements.

The filtering circuit 132 can be connected to the signal amplifying circuit 131 for filtering the electrical signal amplified by the signal amplifying circuit 131. Corresponding parameters of the filtering circuit 132 can be set to filter signals having undesired frequencies and obtain needed electrical signals, for example, to filter the signal having a frequency not in the range from 0.7 Hz to 3 Hz and to obtain the needed heartbeat signal (generally having a frequency ranging from 0.7 Hz to 3 Hz). Thus, corresponding parameters of the filtering circuit 132 can be set to allow the filtering circuit 132 to filter undesired electrical signals and obtain needed physiological signals.

The A/D conversion circuit 133 can be connected to the filtering circuit 132 for performing the analog-to-digital conversion to the filtered electrical signal. Since the electrical signal generated by the tensile force sensor 12 is generally an analog signal, the filtered electrical signal is correspondingly an analog signal. The A/D conversion circuit 133 is capable of converting the analog signal to a digital signal for allowing for easy operations such as a further process and transmission of the signal.

In order to improve the convenience of the collection of the human body physiological signal, the collection of the physiological signal can be separated from a further analysis and unified storage of the physiological signal. After the needed physiological signal is collected, the wireless through transmission circuit 14 can transmit the physiological signal to a remote device to allow for the further analysis and unified storage of the physiological signal.

The above device further includes a power supply unit (not shown) and a power supply management unit (not shown). The power supply unit is configured for supplying power and the power supply management unit is configured for managing the power supply unit.

The above power supply unit can be a battery for supplying power to the above device. The device manages the power supply unit via the power supply management unit.

The above power supply unit can be a connecting component connected to an external power supply for supplying power to the above device. The above device manages the connecting component via the power supply management unit.

The above physiological signal collecting mattress converts the human body pressure to an electrical signal and processes the electrical signal via the wavy flexible body 11, thereby obtaining the human body physiological signal without directly contacting human skin, allowing the physiological signal to be obtained more conveniently. Meanwhile, the obtained physiological signal is transmitted to a remote device by using wireless technology to separate the collection of the signal from the further analysis and unified storage of the signal, which further facilitates the collection of the physiological signal.

Even though information and the advantages of the present embodiments have been set forth in the foregoing description, together with details of the mechanisms and functions of the present embodiments, the disclosure is illustrative only; and that changes may be made in detail, especially in matters of shape, size, and arrangement of parts within the principles of the present embodiments to the full extend indicated by the broad general meaning of the terms in which the appended claims are expressed.

What is claimed is:

1. A wavy physiological signal collecting device, comprising: a wavy flexible electrode, comprising a flexible panel and a plurality of flexible protrusions each of which is arranged on the flexible panel for converting a human body pressure applied thereto to a tensile force; wherein the flexible protrusions are respectively spacedly arranged on an upper surface and a lower surface of the flexible panel to form a panel of the wavy flexible electrode, a spacing area is defined between two adjacent flexible protrusions; each flexible protrusion located on the upper surface corresponds to a spacing area between two adjacent flexible protrusions arranged on the lower surface, and each spacing area located on the upper surface corresponds to a flexible protrusion located on the lower surface; the flexible protrusion and the spacing area are in one-to-one correspondence in corresponding areas on the upper surface and the lower surface of the flexible panel; a tensile force sensor arranged in the flexible panel for generating an electrical signal according to the tensile force; and a signal processing unit configured for processing the electrical signal to obtain a corresponding human body physiological signal; wherein a cross-sectional view of each of the flexible protrusions is a curved surface, and curved surfaces of the flexible protrusions located on the upper surface cooperating with curved surfaces of the flexible protrusions located on the lower surface to form a sinusoid symmetrically centered on the flexible panel; and the tensile force sensor is only arranged in the spacing area between two adjacent flexible protrusions.

2. The device of claim 1, wherein the signal processing unit comprises a signal amplifying circuit for amplifying an analog electrical signal, a filtering circuit for filtering the amplified analog electrical signal to obtain the human body physiological signal, and an A/D conversion circuit for converting the filtered analog electrical signal to a digital signal.

3. The device of claim 1 further comprising a wireless through transmission circuit configured for transmitting the digital signal through wireless unvarnished transmission.

4. The device of claim 1 further comprising a power supply unit for supplying power and a power supply management unit for managing the power supply unit.

5. The device of claim 4, wherein the power supply unit comprises a battery.

6. A physiological signal collecting mattress, comprising at least two wavy physiological signal collecting devices and a wireless through transmission circuit; each of the wavy physiological signal collecting devices comprising: a wavy flexible electrode, comprising a flexible panel and a plurality of flexible protrusions each of which is arranged on the flexible panel for converting a human body pressure applied thereto to a tensile force; wherein the flexible protrusions are respectively spacedly arranged on an upper surface and a lower surface of the flexible panel to form a panel of the wavy flexible electrode, a spacing area is defined between two adjacent flexible protrusions; each flexible protrusion located on the upper surface corresponds to a spacing area between two adjacent flexible protrusions arranged on the lower surface, and each spacing area located on the upper surface corresponds to a flexible protrusion located on the lower surface; the flexible protrusion and the spacing area are in one-to-one correspondence in corresponding areas on the upper surface and the lower surface of the flexible panel; a tensile force sensor arranged in the flexible panel for generating an electrical signal according to the tensile force; and a signal processing unit configured for processing the electrical signal to obtain a corresponding human body physiological signal; and the wireless through transmission circuit configured for transmitting the electrical signal through wireless unvarnished transmission; wherein a cross-sectional view of each of the flexible protrusions is a curved surface, and curved surfaces of the flexible protrusions located on the upper surface cooperating with curved surfaces of the flexible protrusions located on the lower surface to form a sinusoid symmetrically centered on the flexible panel; and the tensile force sensor is only arranged in the spacing area between two adjacent flexible protrusions.

7. A physiological signal collecting mattress, comprising at least two wavy physiological signal collecting devices and a wireless through transmission circuit; each of the wavy physiological signal collecting devices comprising: a wavy flexible electrode, comprising a flexible panel and a plurality of flexible protrusions each of which is arranged on the flexible panel for converting a human body pressure applied thereto to a tensile force; wherein the flexible protrusions are respectively spacedly arranged on an upper surface and a lower surface of the flexible panel to form a panel of the wavy flexible electrode, a spacing area is defined between two adjacent flexible protrusions; each flexible protrusion located on the upper surface corresponds to a spacing area between two adjacent flexible protrusions arranged on the lower surface, and each spacing area located on the upper surface corresponds to a flexible protrusion located on the lower surface; the flexible protrusion and the spacing area are in one-to-one correspondence in corresponding areas on the upper surface and the lower surface of the flexible panel; a tensile force sensor arranged in the flexible panel for generating an electrical signal according to the tensile force; and a signal processing unit configured for processing the electrical signal to obtain a corresponding human body physiological signal; the flexible electrode being configured as a piece and the flexible panel and the flexible protrusions being integrally formed; the flexible panel being elongated and at least comprising an upper surface and a lower surface, and the flexible protrusions being respectively arranged on the upper surface and the lower surface; and the unvarnished transmission circuit configured for transmitting a digital signal of the electrical signal through unvarnished transmission; wherein a cross-sectional view of each of the flexible protrusions is a curved surface, and curved surfaces of the flexible protrusions located on the upper surface cooperating with curved surfaces of the flexible protrusions located on the lower surface to form a sinusoid symmetrically centered on the flexible panel; and the tensile force sensor is only arranged in the spacing area between two adjacent flexible protrusions.

* * * * *